United States Patent
Menzel et al.

(10) Patent No.: US 9,259,298 B2
(45) Date of Patent: Feb. 16, 2016

(54) DENTAL IMPLANT SYSTEM

(71) Applicant: Dental Service Center Michael Menzel GmbH, Goerlitz (DE)

(72) Inventors: Michael Menzel, Goerlitz (DE); Henning Roerup, Amelinghausen (DE); Konstantinos Arapoglou, Karlsruhe (DE)

( * ) Notice: Subject to any disclaimer, the term of this patent is extended or adjusted under 35 U.S.C. 154(b) by 43 days.

(21) Appl. No.: 13/705,280

(22) Filed: Dec. 5, 2012

(65) Prior Publication Data
US 2013/0095451 A1    Apr. 18, 2013

Related U.S. Application Data

(62) Division of application No. 12/596,372, filed on Jun. 23, 2010, now abandoned.

(30) Foreign Application Priority Data

Apr. 17, 2007  (DE) .......................... 10 2007 018 453
Apr. 2, 2008   (DE) .......................... 10 2008 017 085
Apr. 2, 2008   (DE) .......................... 10 2008 017 086

(51) Int. Cl.
*A61C 8/00*   (2006.01)
*A61K 6/02*   (2006.01)
*A61K 6/04*   (2006.01)

(52) U.S. Cl.
CPC ............... *A61C 8/0075* (2013.01); *A61C 8/005* (2013.01); *A61C 8/0018* (2013.01); *A61C 8/0077* (2013.01); *A61K 6/024* (2013.01); *A61K 6/04* (2013.01)

(58) Field of Classification Search
CPC ...... A61C 8/00; A61C 8/0018; A61C 8/0036; A61C 8/0037
USPC .............................. 433/172–176, 201.1, 215
See application file for complete search history.

(56) References Cited

U.S. PATENT DOCUMENTS

| | | | |
|---|---|---|---|
| 4,279,598 A * | 7/1981 | Scheicher | 433/173 |
| 4,964,801 A * | 10/1990 | Kawahara et al. | 433/173 |
| 6,250,922 B1 * | 6/2001 | Bassett et al. | 433/172 |
| 2005/0015154 A1 * | 1/2005 | Lindsey et al. | 623/23.46 |
| 2005/0026114 A1 * | 2/2005 | Nilo et al. | 433/173 |
| 2005/0100864 A1 * | 5/2005 | Elian | 433/173 |

* cited by examiner

*Primary Examiner* — Heidi M Eide
(74) *Attorney, Agent, or Firm* — Patricia Mathers (57) ABSTRACT

Dental implant system for mounting a dental superstructure is disclosed. Enossal, gingival, transgingival sections plus implant head are integrated into a single-piece implant body. The enossal and gingival sections have geometries derived from diagnostic patient data and, thus, correspond geometrically precisely to the shape of the patient's jawbone and the drilled implant cavity, completely filling those portions of the cavity. The superstructure covers the entire surface of the implant head, filling out the rest of the cavity. The surface structure of the dental implant has no gaps in it and portions of it are textured so as to facilitate complete fusing of tissue to implant, thereby preventing formation of gum pockets. Sections of the dental implant are rotationally asymmetrical, so as to ensure proper location of the implant in the cavity and prevent rotation. The construction of the implant also prevents the occurrence of micro-movements.

18 Claims, 5 Drawing Sheets

DENTAL IMPLANT SYSTEM

FIELD OF THE INVENTION

The invention refers to a dental plant system comprising an implant and a superstructure.

BACKGROUND INFORMATION

Description of the Prior Art

Around 700,000 artificial tooth replacements are implanted each year in Germany. Usually, this replacement involves three components: an artificial root (root implant), a connecting piece, the so-called abutment, and a superstructure, such as a crown or bridge.

In order to implant the artificial tooth replacement, it is first necessary to remove all remains of the defective tooth, for example, its roots. Subsequently, a hole is drilled into the jaw bone and possibly provided with a screw thread, prior to the root implant being driven or screwed into this hole. The implant thus usually takes the form of a cylinder or taper. After implantation into the jaw, the implant must be left to heal for three to six months, so that it fuses with the jaw bone. During this period, the implant must not be subjected to mechanical loads. After healing, the usual practice is to screw or bond the abutment to the implant, and subsequently to mount the superstructure on the abutment. The abutment incorporates a so-called abutment post, which serves to mechanically fasten the superstructure on the abutment.

This method, however, has several disadvantages. Inherent to the design is the formation of a gap between the implant and the abutment, the gap being susceptible to bacteriological colonization. Periodontal pockets along the abutment in the direction of the bone provide open portals of entry for bacteria. The acid waste products excreted by the bacteria hinder the fusing of the gingiva with the implant/abutment in the region of the gap. The jaw bone continuously regresses in accordance with the biological width; gingivitis and further bone loss, as well as subsequently further gingival loss often occur. A consequence thereof is the formation of bacterial pockets. Because the pockets are not accessible to the patient himself, they require expensive and for the patient annoying dental recall measures to clean the affected pocket of bacteria and regularly also lead to loss of the implant. Cleaning the pocket further results in the gingiva not being able to fuse with the abutment in the region above the gap between the abutment and the implant. Furthermore, the temporarily unavoidable restricted accessibility of the periodontal pockets hinders proper oral hygiene in this region. As a result, the patient considers the implant to be very unpleasant. During this time, the inflammation and destruction of healthy tissue progresses further.

A further disadvantage is that the threaded connections between root implant and abutment are subjected to high mechanical loads. As a result, micro-movements regularly occur between the implant and the abutment, which, in the long run, lead to breakages of the screw with resulting high costs. If the threaded connection is fixed with cement or adhesive, moreover, cement or adhesive oozing from the connection may lead to irritation of the gingiva.

The root implants are generally constructed as prefabricated, rotationally symmetrical standard implants in various graduated sizes. CE standards on the sterilization of medical articles do not permit the dentist performing the implantation to individually adapt the prefabricated implant during the implantation process. The given size graduation, therefore, often requires that compromises be accepted with regard to the size of the implant used. It is a further disadvantage that the implant cannot be matched or adapted to bone dehiscences that arise when drilling the implant bed in the ridge-form jaw bone. As a result, such implants have a significantly reduced bone contact area and, consequently, provide poorer anchoring, than would be possible with individual adaptation. Furthermore, the anatomical soft-tissue demands of the gingiva are not taken into account. Aesthetics and hygiene are thus greatly impaired. Uncompensated bone dehiscences are regularly the cause of the formation of undesirable periodontal pockets. Finally, high inventory costs are incurred, because the prefabricated standard implants must be kept in inventory in many sizes and forms.

The fixing of the superstructure to the abutment by means of an abutment post leads to unfavorable force distributions and lever ratios, resulting in turn in an increased risk of breakage. Furthermore, it has been proven that thread-fastened abutment posts result in additional destructive micro-movements.

Over the past years, considerable advances have been achieved in dental implantology; numerous developments are aimed at overcoming the above-mentioned problems.

In DE 196 47 489 A1, it is proposed to apply a directly plated, plastically formable metal layer to the abutment at the point of contact to the enossal implant body. The intention is to avoid the formation of a gap between abutment and implant that is susceptible to bacteriological colonization. Analogously, DE 196 47 490A1 suggests the inclusion of a gold disc between the implant and the implant mount. It is true that both solutions achieve a minimization of the gap, but it is foreseeable, that the contact between titanium, gold and gingiva, as well as saliva will trigger irritating chemical reactions. Bacteriological colonization, furthermore, cannot be excluded.

WO2004/058096 A1 describes an abutment which is provided with an axial through-hole. It is proposed to screw fasten the abutment to the implant, the screw fastening being fixed in addition with cement. The through-hole serves to enable excess cement to be pressed out through it during the cementing, so that the excess cement collects on the flat head of the implant. The cement can then be removed simply from the head. In this way, gingivitis caused by cement extruding at other places can be prevented.

DE 10 2005 027 402 A1 discloses a method of producing an individualized replacement tooth, which can be mounted into a healed implant by means of a connecting stub. To reduce the cost of producing the dentures, it is proposed to produce the replacement tooth as a single piece. In this manner, it is possible to dispense with a separate abutment. It is not to be disputed that this achieves a simplification; the problem of a gap susceptible to bacteriological colonization, however, remains.

EP 0 967 931 B1 discloses a dental implant which comprises a tapered shaft section and a divergent head section, wherein both sections are formed integrally or produced as a compound part. The dental implant system covers furthermore an abutment that fits the dental implant and that serves to support a denture or crown. The abutment is screwed into the tapered shaft section of the implant by means of a screw.

The single component or integrated construction of the shaft and head section does indeed avoid a micro-gap in the enossal area, but it is still inevitable that a gap form between the shaft/head section and the abutment in the gingival region, the gap being susceptible to bacteriological colonization.

EP 0 891 163 B1 describes a dental support structure that is constructed of an implant and an abutment. The upper edge of the abutment and, correspondingly, the lower edge of the crown affixed to the abutment are adapted at the point of emergence from the gingiva to the corresponding exit profile and the dimensions of the tooth to be replaced.

The adaptation of the boundary between the abutment and the crown with the profile of the gingiva achieves aesthetic and functional advantages over rotationally symmetrical solutions. The boundary between the abutment and the crown, however, lies exactly at the height of the gingival margin or above the same. Because the gingiva usually recedes over the course of time, it is unavoidable that, with time, the metallic abutment will protrude beyond the gingival margin and become visible.

Alternatively to the above-described dental replacement, the general state of the art uses a rotationally symmetrical implant wherein the enossal parts of the implant, the abutment and, if applicable, the abutment posts are constructed from a single piece or at least seamlessly joined (see DE 10 2005 001 185 A1).

Such implants thereby avoid a gap in the boundary region between jaw bone and gingiva from the beginning and the gingiva is able to fuse with the implant without problems, because micro-movements are avoided. Even so, these implants have not been able to assert themselves for several essential reasons. One reason is the fact that the abutment post, as a result of the design, protrudes into the mouth. This leads inevitably to mechanical loads on the implant during the period of fusing with the surrounding tissue and, consequently, frequently to failure of the implantation. A further reason is the fact that, due to the rotational symmetry of the implant, the implant remains visible at the transition from crown to gingiva. This is not acceptable from an aesthetic point of view, particularly when using titanium. It is especially disadvantageous that the form of the implant does not take into consideration the vestibular/buccal and palatinal/lingual bone dehiscences that are caused by drilling into the ridge-form jaw bone.

BRIEF SUMMARY OF THE INVENTION

The goal of the invention is to overcome the disadvantages in the prior state of the art. In particular, the goal is to create an aesthetically appealing dental implant system which remains invisible at the gingival margin, enables good fusing with the gingiva in the gingival region, and guarantees a mechanically stable and long-lasting connection between a dental abutment and the jaw bone.

The goal is achieved according to the invention by the characteristic features of any independent claim. Further advantageous embodiments are derived from the dependent claims.

The starting point is a dental implant system comprising an implant and a superstructure constructed thereupon. The implant comprises a lower enossal section constructed typically as a honeycomb or threaded structure, an upper enossal section which widens towards the top and with a roughened surface, a transgingival section with a smooth wall, and a transgingival implant head. All of these sections adjoin each other seamlessly and without gaps.

The lower enossal section is usually formed to be rotationally symmetrical and cylindrical/tapered; or a combination rotationally symmetrical and rotationally cylindrical/tapered, rotationally symmetrically stepwise cylindrical/tapered; or a combination rotationally symmetrical, stepwise cylindrical/tapered. Preferably, the lower enossal section is provided with a honeycomb texture or structure with pointed protrusions at the corner points, which is known for its good fusing into the jaw bone.

According to the invention, the upper enossal section displays a shortening in both the vestibular/buccal and palatinal/lingual directions. Accordingly, the upper enossal section is constructed to be higher at points where it laterally abuts the jaw ridge. In this way, the shape of the implant is matched precisely to the patient-specific jaw ridge shape, and the implant fully accommodates any bone dehiscences that arise from drilling the implant bed. The outward flare of the upper enossal section towards the upper edge, i.e., toward the gingiva, provides a greater contact area with the bone for implantation and, consequently, provides a better hold for the implant in the jaw bone.

The smooth transgingival section is shaped according to the cavity in the patient's gingiva. As a result of this anatomical shaping, the transgingival section has a different shape in any longitudinal or cross-sectional plane from that of any preceding or subsequent longitudinal or cross-sectional plane.

The transgingival section is limited toward the upper edge by an individually formed transgingival implant head, the shape of which is differentiated three-dimensionally in height, width and depth, i.e. the implant head represents the "lid surface" of the implant. Its form in any longitudinal or cross-sectional plane similarly differs from each corresponding previous or subsequent longitudinal or cross-section plane. The peripheral edge formed in this way by the transgingival section and the transgingival implant head corresponds hereby to the preparation boundary and is shaped such that, following implantation, it runs slightly, typically 1 mm, below the gingival margin.

The transgingival implant head displays a flat portion at its center. This is surrounded by a portion which drops off more steeply and connects the flat portion with the transgingival section of the implant. The plateau formed by the flat portion of the implant head is hereby disposed to be exactly so high, that its height lies precisely at the height of the upper gingival boundary in the approximal direction.

Due to the adaptation of the upper enossal section to the patient-specific shape of the jaw ridge, the steeper portion of the implant head is longer and steeper in the vestibular/buccal direction as well as in the palatinal/lingual direction than in the other directions.

A superstructure is glued or cemented onto the whole area of the implant head by means of its underside, which is adapted to the shape of the implant head. This adhesive connection takes up the majority of the forces exerted between the implant and the superstructure. To prevent lateral shifting and to achieve further mechanical stabilization, an abutment post or mounting post is additionally screwed into the transgingival section of the implant approximately at the center of the preparation area and connected or adjoined on its other end with the superstructure. The basal surface of the abutment post lies on the flat portion of the transgingival implant head and acts as a force-compensating tilt-prevention feature and as a component to take up and distribute forces.

The implant is advantageously produced from a single piece, i.e., a blank. Suitable materials proven for medical applications such as this are titanium and zirconium dioxide, as well as all materials suitable for dental implantation.

The dental implant system according to the invention displays several advantages compared to the systems normally used.

An essential advantage of the implant system is that it dispenses with an abutment. This means a priori that formation of a gap that is susceptible to bacteriological colonisation in the boundary region between jaw bone and gingiva is avoided. Because the preparation boundary lies just below the gingival margin, it is accessible for the patient and can be cleaned conveniently by the patient. This eliminates the necessity of pocket cleanings by the dentist. Moreover, the implant is even able to fuse together with the gingiva in the transgingival section, at the same time the enossal section is fusing with the jaw bone. This is particularly advantageous when the gingiva is still "fresh and bloody" from the implantation procedure. Because it is not necessary to clean pockets, it is later also not necessary to detach gingiva which has already fused to the implant. As a result, expensive and for the patient annoying recall measures are avoided and moreover, because periodontal pockets are not formed as would otherwise be the case, the implant is also not perceived as a foreign body by the patient, because the oral hygiene measures in this area can be performed simply and above all reliably.

The elimination of the threaded joint between implant and abutment excludes micro-movements between implant and abutment, which are otherwise inherent in the construction of the implant and are frequently the cause not only for the breaking of the screw, but also for regression of the surrounding portions of the jaw bone and subsequently furthermore for regression of the gingiva which lies over the jaw bone and is supported and stabilized by that bone.

The individual size and shape of the lower enossal section, which is adapted to the anatomy of the patient, achieves the largest possible bone contact area. The upwardly widening form as well as the precise adaptation of the upper enossal section to the ridge form of the jaw bone, and the resulting full adaptation to the bone dehiscences that result from the drilling of the implant bed, similarly ensures a large area of contact in the upper portion of the jaw bone. Due to its structured and rough surfaces, the enossal section of the implant is able to fuse quickly and reliably with the jaw bone.

The only joint location of the dental implant system has been chosen such that, on the one hand, it can be cleaned by the patient himself, while on the other hand, mechanical stresses due to mechanical contact, e.g. with other teeth, are nevertheless for the most part avoided during the healing phase.

Contrary to dental implant systems used to date, in which the mechanical connection between implant and superstructure is achieved predominantly by means of an abutment/abutment post, in the system according to the invention, a large-area, positive-mating material connection, formed by glue or cement between implant head and the underside of the superstructure, takes up the mechanical loads. The prosthetic post used has a supporting function, prevents lateral shifting during mounting of the superstructure and, through the basal contact on the flat portion of the transgingival implant head, acts as an element to take up laterally incident forces that may occur.

In accordance with the invention, it is also proposed to shape the lower and upper enossal sections of the dental implant system such that they are rotationally asymmetrical, wherein the geometry corresponds to the superimposition of at least two rotationally symmetrical bodies, whose axes of symmetry are vertically parallel to each other or else tilted relative to each other, such that they intersect at least in the upper enossal section. The geometric bodies always overlap each other at least in the upper enossal section, so that integral, rotationally asymmetrical cross-sectional areas are formed there. The lower enossal section can be formed like the root of a tooth or also display similarly integral cross-sectional areas.

Due to the rotationally asymmetrical shape of the enossal section, the inserted implant and the jaw bone form an abutment that is able to withstand relatively high torsional and tilting loads. In addition, this embodiment enables an unambiguous positioning and fixing of the implant in the jaw bone.

For the parts of the upper and lower enossal sections, which display integral cross-sectional areas, geometries which correspond to the superimposition of cylindrical geometric bodies and conical protrusions are preferably selected. The cylinders may possess identical or different radii. The axes of symmetry of the bodies are arranged such that they intersect at least in the upper enossal section. The angle of tilting of the axes of symmetry to each other is usually between 1° and 45°.

For parts of the lower enossal section that are formed like the root of a tooth, geometries which correspond to the superimposition of conical geometric bodies arranged parallel to each other are preferably selected.

The method to manufacture the dental implant system and to introduce the same into the jaw or mouth of the patient encompasses the following steps:

First, the shape of the jaw and the shape of the gingiva of the patient to be treated are recorded by means of CT (computer tomography), DVT (volume tomography) or, alternatively, by means of an OPG.

On a blank from which the whole implant is to be produced, the enossal section is first shaped on the basis of the determined anatomical diagnostic data with the aid of CAD/CAM technology. This section is shaped so as to be rotationally symmetrically cylindrical/tapered, or combined rotationally symmetrically cylindrical/tapered, rotationally symmetrically stepwise cylindrical/tapered, or combined rotationally symmetrically stepwise cylindrical/tapered. To enable good fusing into the bone, the enossal section is provided with a textured surface. The preferred choice is hereby a proven honeycomb texture with points or protrusions at its corner points.

Subsequently, a further enossal section that adjoins the enossal section, which corresponds to the anatomical diagnosis data, is formed by means of CAD/CAM. A slope is hereby incorporated in the vestibular/buccal direction and a lesser slope in the palatinal/lingual direction, in order to adapt the enossal section to the individual shape of the jaw ridge. In this way, bone dehiscences that occur later from drilling the implant bed are fully accommodated by the shape of the implant.

After that, a transgingival section is produced by manual working or possibly by means of CAD/CAM on the basis of the determined anatomical diagnostic data. The individual shaping results in each longitudinal plane and each cross-sectional plane of the transgingival section always possessing a shape that differs from each corresponding previous or subsequent longitudinal or cross-sectional plane.

Then, the transgingival implant head that is the upward limitation of the transgingival section is produced by manual working or possibly by means of CAD/CAM. The implant head is shaped according to the diagnostic survey data pertaining to the form and edge contour of the cavity in the gingiva, such that edge formed by the preparation area and the transgingival section runs below the gingival margin after implantation. A flat portion is formed approximately in the center of the implant head, surrounded by a portion which drops off more steeply. The steeper portion connects the flat portion and transgingival section. Furthermore, a threaded bore for receiving an mounting post is drilled into the flat portion of the implant head.

Next, the transgingival section and the transgingival implant head are smoothed. The smoothing is done preferably by manual mechanical polishing or by CAD/CAM. Thereafter, the surface of the whole enossal section of the implant is roughened by means of suitable techniques.

The next step is to approach stepwise the diameter of the implant bed to be drilled. To this end, the implant bed is first drilled into the jaw bone step by step using corresponding drill bits, beginning with a diameter approx. 1 mm smaller and progressing to a diameter 0.5 mm smaller than the lower enossal section of the implant. Subsequently, the hardness and quality of the bone is determined, based on the drilled hole or by further test procedures. The bone quality and hardness may change dramatically while enlarging of the drilled hole. For this reason, the diameter of the drilled hole is increased gradually in steps of 0.1 mm. The bone quality is determined once more after each drilling step and the diameter of the drilled hole checked with the aid of suitable measuring instruments and methods. The drilled hole is enlarged further step by step until the bone quality and the size of the drilled hole are matched optimally to each other.

Then, the implant is inserted by driving the enossal section into the drilled hole.

Subsequently, the implant heals and fuses into the jaw over a period of 3 to 6 months.

In a further step, a suitable mounting post is selected or manufactured. If the implant displays no angulation, then it is possible to use a straight, prefabricated mounting post with a thread on one end to permit it to be screwed into the transgingival implant head and a post for fixing to the superstructure on the opposite end. Should angulation occur, a sleeve of mold plastic is shaped individually, either subtractively by means of mechanical attrition or additively by applying wax. The resulting model is subsequently cast in metal according to the disposable pattern method, whereby a screw is inserted through the sleeve in the longitudinal direction and the post sleeve screwed to the transgingival implant head by means of this screw. Alternatively, the mounting post may also be produced wholly by means of CAD/CAM.

Furthermore, a superstructure matched individually to the diagnostic data of the patient is produced, e.g. a crown or bridge. When doing so, the underside of the superstructure, which serves as the contact surface to the implant, can be formed on the basis of the already available geometric data of the preparation boundary when shaping the edge, and by means of the inverted data of the surface of the implant head when shaping the topology of the underside surface.

Once the implant has healed and fused into the jaw, the mounting pas screwed into the threaded hole in the implant head.

Subsequently, the underside of the superstructure which has been formed to correspond to the shape of the implant head is glued or cemented to the entire surface of the implant head. In the same step, the mounting post is mechanically connected with the superstructure.

BRIEF DESCRIPTION OF THE DRAWINGS

In the following, the invention is explained in more detail by way of four embodiments.

DETAILED DESCRIPTION OF THE INVENTION

Figure 1:
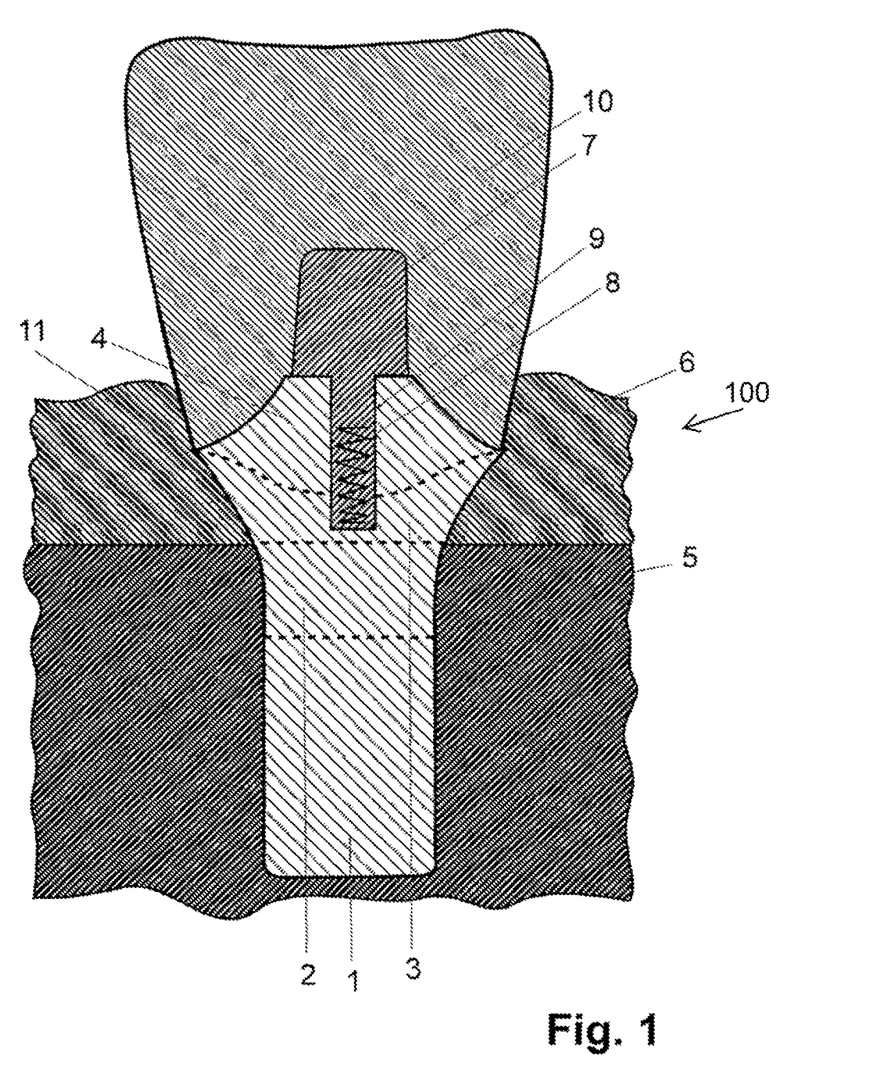
FIG. 1 is a cross-sectional view of a dental implant according to the invention, with a crown mounted on the implant, shown from the vestibular side.
Figure 2:
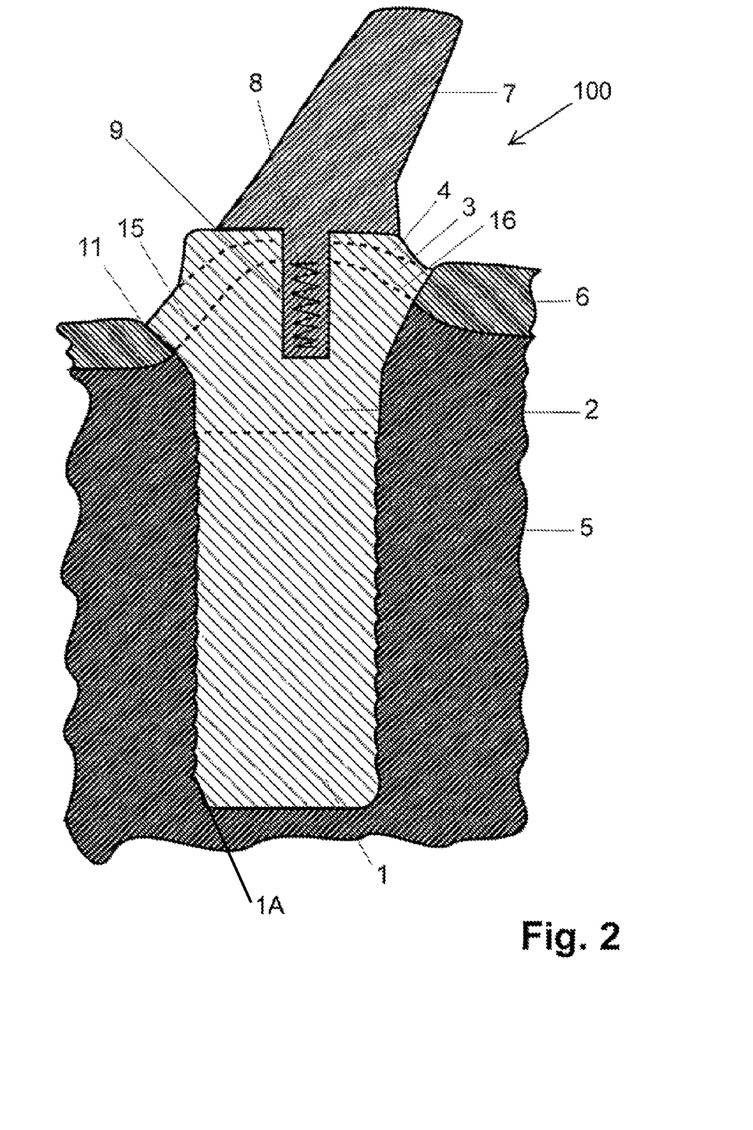
FIG. 2 is a cross-sectional view of a dental implant, without the crown, shown from the approximal side.

FIG. 1 shows the cross-section, viewed in the palatinal direction, of a one-piece dental implant 100 made of titanium, with a crown 10 fixed to the implant 100. For better illustration, FIG. 2 shows a cross-section of the implant 100 with a prosthetic mounting post 7, but viewed in the direction of the jaw bone.

The implant comprises a lower enossal section 1, an upper enossal section 2, a transgingival section 3 and a transgingival implant head 4. To manufacture the implant, section 1 and section 2 are formed by means of a CAD/CAM, and section 3 and the transgingival implant head 4 either by means of a CAD/CAM or by manual working of a blank.

The lower enossal section 1, which sits deep within the jaw bone, has a honeycomb structure 1A on its surface, with protrusions in each of the corners of the honeycomb. This proven structure permits optimal fusing of the implant 100 into the bone.

The upper enossal section 2, which is shaped such that its upper edge aligns exactly with the edge of ridge-form jaw bone 5, adjoins the lower enossal section 1. To achieve this, the upper enossal section 2 is usually formed with a vestibular/buccal slope or shortening 15 on the vestibular side and a palatinal/linguale slope or shortening 16 on the palatal side. The vestibular slope 15 is significantly shorter and the palatinal shortening 16 somewhat shorter on the palatinal side than all other points on the upper enossal section 2. There are also cases, however, in which the palatinal side must be formed shorter than the vestibular side to achieve precise adaptation to the ridge form of the jawbone. This special shaping of the implant 100 accommodates fully and anatomically any bone dehiscences that result from the drilling of the implant bed. Furthermore, the upper enossal section 2 flares outward at the upper end in a funnel shape, in order to achieve a broader contact area and a better force distribution in the bone 5. The section 2 is also able to fuse with the jaw bone 5, because of its textured or roughened surface.

The smoothly polished transgingival section 3 follows section 2. This section is formed such, that it extends circumferentially approx. 1 mm below the gingival margin. This corresponds approximately to the depth to which the gingiva is not fused with the tooth, even a healthy tooth, but instead merely loosely abuts the tooth. The smoothly polished titanium surface hereby enables good and irritation-free fusing of the gingiva 6.

The transgingival implant head 4 adjoins the end of the transgingival section 3, which at the same time forms a preparation boundary 11. The implant head 4 comprises a flat, almost level inner portion 12 and a slanted portion 13 that surrounds the inner portion 12; the portions 12/13 (shown in FIG. 3) may also be formed without a transition, i.e., for example, be somewhat ball-shaped. The slanted portion 13 connects the flat portion 12 with the transgingival section 3. Because the implant 100 is adapted to the ridge form of the jaw bone 5, the portion 13 is usually significantly longer and steeper in the vestibular/buccal direction and only somewhat longer and steeper in the palatinal/lingual direction than in the other directions.

Figure 3:
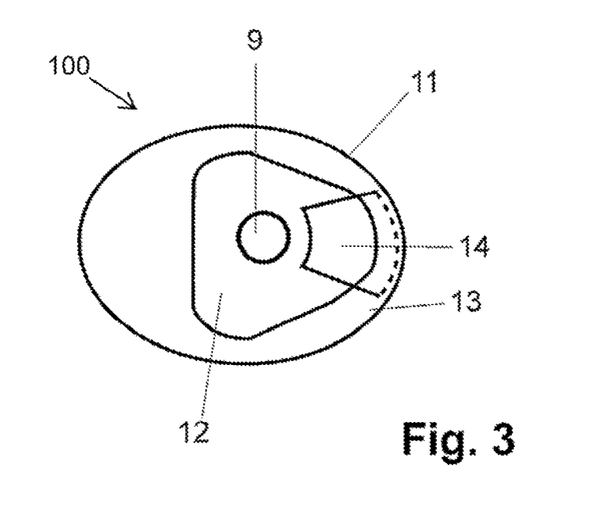
FIG. 3 is a top plane view of a dental implant according to the invention.

As seen in FIG. 3, there is a threaded bore 9 having threads 8 in the flat portion 12 of the implant for the purpose of fastening a prosthetic mounting post 7 (shown in FIGS. 1 and 2). Furthermore, a keying recess 14 is provided in the portion 12 in the form of a partial circular segment, to prevent rotation of the crown. To this end, a corresponding mating element is formed on the underside of the crown 10. As seen in FIG. 2, an individually manufactured prosthetic mounting post 7 is used. This post also engages in the recess 14 and is thus also secured against rotation. If a straight, standardized mounting post 7 is used, then this post does not engage in the recess 14. Instead, its post portion is merely bevelled. This ensures that, when the post 7 is later cemented into the crown 10, which is in turn affixed to the implant 100 and secured against rotation via the recess 14 and the actual form of the implant head 4 up to the preparation boundary 11, the post 7 is then fastened to the crown 10 and secured against rotation.

The underside of the crown 10, which serves as the transition to the implant 100, is adapted to fit precisely to the shape of the implant head 4 down to the preparation boundary 11. It is an advantage that the already available geometric data of the preparation boundary 11 can be used for forming the edge of the underside, and the inverted geometric data of the implant head 4 can be used for manufacturing the surface of the underside.

The complete surface of the underside of the crown 10 thus shaped is bonded with cement or glue with the transgingival implant head 4, gap-free. Any material oozing out during gluing or cementing can easily be removed, given the good accessibility of the preparation boundary 11. In addition, the smooth part of the prosthetic mounting post 7 is cemented into the crown 10. The mounting post 7 is screwed into the implant head 4 with its other end, which is formed as a screw. The complete surface bonding between the crown 10 and the implant 100 takes up a large proportion of the forces that occur during chewing. The connection via the prosthetic post 7 and the contact surface area on the flat portion 12 of the implant head 4 serve to prevent lateral shifting and assist in taking up and distributing shear forces.

Embodiments of the invention with regard to the enossal section are shown in FIGS. 4 to 7, namely the drilling of the bores in the jaw ridge, which forms the shape of the implant bed and, in the end, determines the geometry of the enossal section of the dental implant system.

Figures 4, 5, 6:
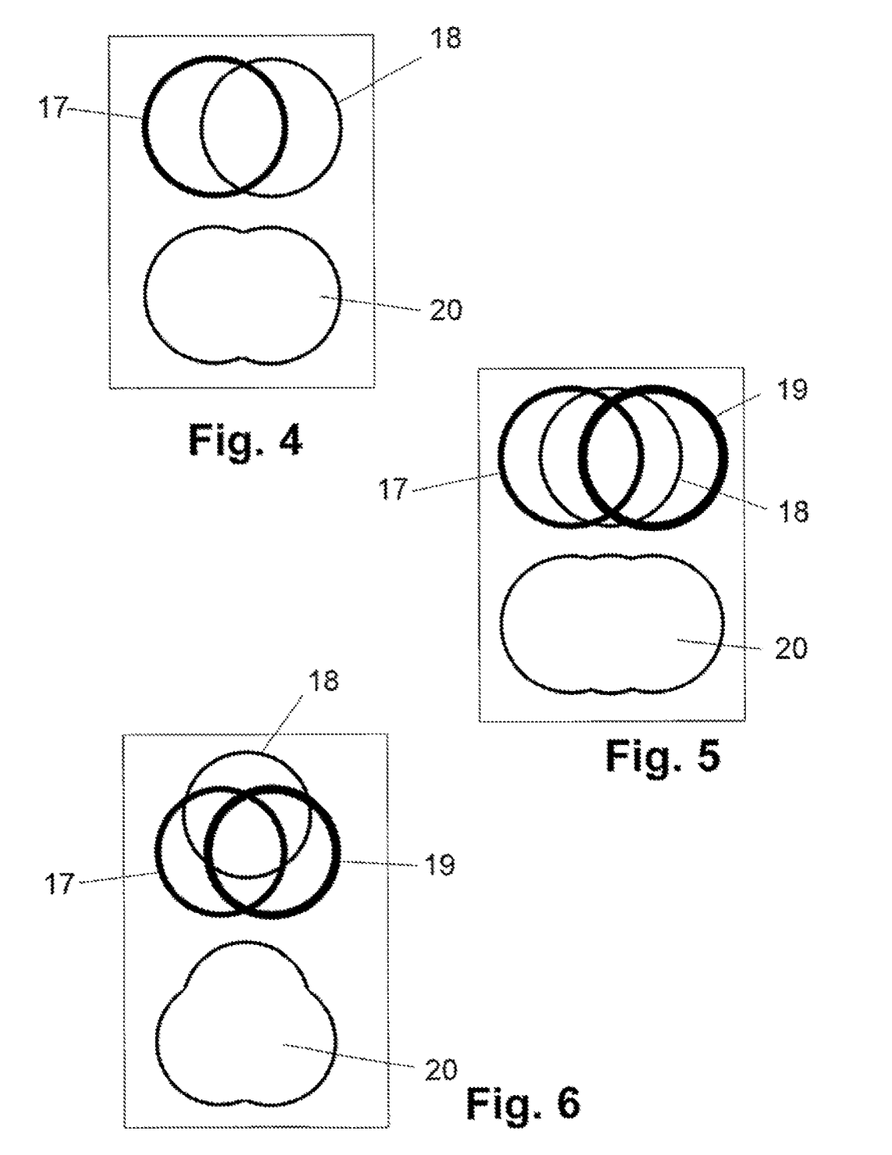
FIG. 4 is a schematic illustration of a first configuration of bores and the resulting shape of the implant bed, shown in top plane view.
FIG. 5 is a schematic illustration of a second configuration of bores and the resulting shape of the implant bed, shown in top plane view.
FIG. 6 is a schematic illustration of a third configuration of bores and the resulting shape of the implant bed, shown in top plane view.

FIGS. 4 to 6 each show in the upper portion of the drawings the positions of the individual holes 17-19 to be drilled for the implant bed and, in the lower portion of the drawings, the form of the implant bed 20 arising from the overlapping of the drilled holes. The drilled holes are cylindrical and all of the same diameter.

FIG. 4 illustrates two overlapping bores, FIG. 5 illustrates three overlapping bores aligned linearly with each other, and FIG. 6 illustrates three bores aligned in the form of an equilateral triangle. The bores 17-19 have been drilled with a defined spacing and tilted towards each other, thereby forming a polygon having n number of edges. The implant bed 20 that is formed by the three drilled bores 17-19 that are spaced apart linearly is capable of withstanding relatively higher torsional loads, whereas the implant bed formed with the three bores 17-19 spaced apart in the configuration of an equilateral triangle is less sensitive to tilting moments.

Figure 7:
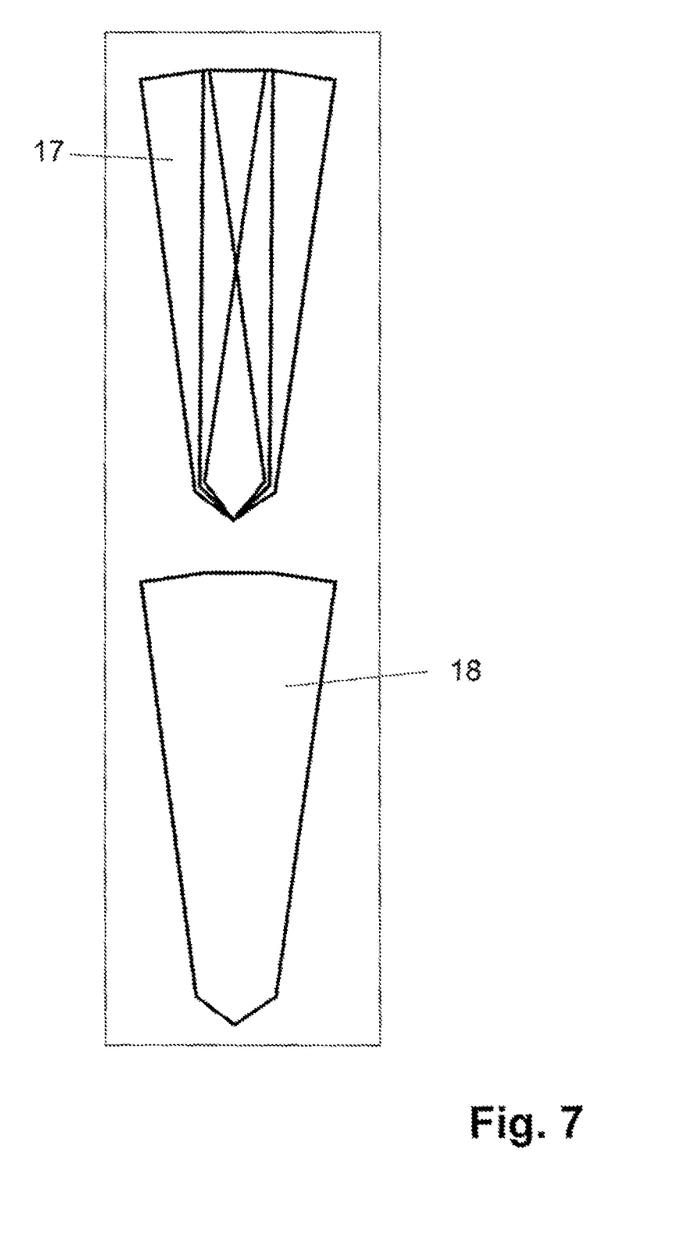
FIG. 7 is a schematic illustration of configuration of bores and the resulting conical shape of the implant bed, shown in side plane view.

FIG. 7 is a schematic illustration of the bores 17-19 in the implant bed 20 and shows that, on the one hand, the tips of the bores 17-19 meet at the lowermost point of the implant bed 20, and, on the other hand, overlap each other over the entire length of the implant bed 20. This produces a conical form of the implant bed 20, and thus of the lower enossal section. In this form, each cross-sectional surface area is continuous.

What is claimed is:

1. A method of forming a cavity and a dental implant for mounting and securing a dental superstructure in the cavity in a jawbone, the cavity serving as an implant bed and having a vestibular/buccal side and a palatinal/lingual side, with a layer of gingiva on the vestibular/buccal side and on the palatinal/lingual side forming an upper limit of the cavity, the method comprising the steps of:
   a) obtaining patient-specific data on a shape of the jawbone and a ridge of the jawbone of a patient;
   b) forming a dental implant that is implantable in the jawbone, the dental implant having a shape that is precisely matched to the patient-specific ridge of the jawbone and having a plurality of sections that include a transgingival implant head, a transgingival section, and enossal sections that include a lower enossal section and an upper enossal section having a wider upper limit;
   c) forming the cavity by drilling a plurality of overlapping holes into the jaw bone, each hole being drilled repeatedly, the overlapping holes formed by an overlap of a plurality of rotationally symmetrical geometric bodies, each geometric body having an axis of symmetry that overlaps with at least one other geometric body at least in a region of the upper enossal section of the dental implant, the geometric bodies being tilted relative each other in a range between 1 and 45 degrees to the vertical, and each drilled hole having a diameter;
   d) determining a quality of the jawbone;
   e) checking the diameter of the drilled hole after each drilling with the aid of suitable measuring instruments and methods; and
   f) gradually increasing the diameter of each drilled hole in steps of 0.1 mm.

2. The method of claim 1, wherein the step of forming the dental implant includes the step of forming the enossal sections to have a rotationally asymmetrical geometry that corresponds to the shape of the cavity.

3. The method of claim 2, wherein the step of forming the dental implant further includes the steps of:
   forming the upper enossal section to have a sloping form that is higher in an area over the ridge in the jawbone, with a downward first slope toward the vestibular/buccal side that corresponds to a slope on the vestibular/buccal side of the jawbone of the specific patient and a downward second slope toward the palatinal/lingual side that corresponds to a slope on the palatinal/lingual side of the jawbone of the specific patient, the first slope and the second slope each terminating at a transition between the upper enossal section and the transgingival section, the transition corresponding to a boundary between the jawbone and the gingiva;
   forming the transgingival section to have an outer shape that is rotationally asymmetrical, such that any cross-sectional plane through the transgingival section has a shape that differs from a shape of any adjacent cross-sectional plane wherein the transgingival section has an upper limit that is bounded by the transgingival implant head, the transgingival implant head having a shape that is differentiated three-dimensionally in height, width and depth;
   defining a preparation boundary on the dental implant that is a circumferential edge and is a transition between the implant head and the transgingival section; and forming the shape of any cross-sectional plane through the transgingival section and the shape of the preparation boundary according to the patient-specific data ascertained from the shape of the cavity in the gingiva and the ridge form of the jawbone, which together determine the gingival contact area on the implant to the gingiva, wherein the dental implant is insertable into the cavity such that the preparation boundary is placed at or slightly below the upper limit of the cavity.

4. The method of claim 3, wherein the step of forming the dental implant includes the step of forming the transgingival implant head to have a flat portion centrally placed, encircled by a sloping portion that connects the flat portion and the transgingival section.

5. The method of claim 4 wherein the flat portion of the transgingival implant head terminates at most 1 mm above the preparation boundary.

6. The method of claim 2, wherein each of the plurality of rotationally symmetrical geometric bodies is cylindrical in form with a cone-shaped tip and wherein the shape of the enossal sections corresponds to a shape obtained when the axes of symmetry of the plurality of rotationally symmetrical geometric bodies intersect in a lower portion of the lower enossal section.

7. The method of claim 1, wherein transitions between the lower enossal section, the upper enossal section, the transgingival section, and the transgingival implant head are formed without any gaps on the outer surface of the dental implant.

8. The method of claim 1, wherein the dental implant is constructed as a single-piece component, with the lower enossal section, the upper enossal section, the transgingival section, and the transgingival implant head being integrated into the single-piece component.

9. The method of claim 1, wherein the implant is made of titanium.

10. The method of claim 1, wherein the implant is made of zirconium dioxide.

11. The method of claim 1, wherein the step of forming the dental implant includes the step of forming a recess in the transgingival implant head, the recess serving to prevent rotation of the dental superstructure.

12. The method of claim 11, wherein the recess has the form of a circular segment.

13. The method of claim 11, wherein the step of forming the dental implant includes the step of engaging a prosthetic abutment pin in the recess.

14. The method of claim 1, wherein the step of forming the dental implant includes the step of providing a texture on an outer surface of the upper enossal section to facilitate a fusion of the jawbone with the dental implant.

15. The method of claim 1, wherein the enossal sections have a surface texture that is not smooth, to facilitate fusion of the jawbone with the dental implant, and the transgingival section has a surface texture that is smooth, to facilitate adhesion of the gingiva with the dental implant.

16. A method of forming a cavity and a dental implant for mounting and securing a dental superstructure in the cavity in a jawbone, the cavity serving as an implant bed and having a vestibular/buccal side and a palatinal/lingual side, with a layer of gingiva on the vestibular/buccal side and on the palatinal/lingual side forming an upper limit of the cavity, the method comprising the steps of:
   a) obtaining patient-specific data from a shape of the jawbone and a ridge of the jawbone of a patient;
   b) forming a dental implant that is implantable in the jawbone, the dental implant having a shape that is precisely matched to the patient-specific ridge of the jawbone and having a plurality of sections that include a transgingival implant head, a transgingival section, and enossal sections that include a lower enossal section and an upper enossal section having a wider upper limit;
   c) forming the cavity by repeatedly drilling a plurality of overlapping holes into the ridge of the jaw bone, the overlapping holes formed by an overlap of a plurality of rotationally symmetrical geometric bodies, each geometric body having an axis of symmetry, wherein the axes of symmetry of the at least two rotationally symmetrical geometric bodies extend parallel to one another, and each drilled hole having a diameter;
   d) determining a quality of the jawbone;
   e) checking the diameter of the drilled hole after each drilling with the aid of suitable measuring instruments and methods; and
   f) gradually increasing the diameter of each drilled hole in steps of 0.1 mm.

17. The method of claim 16, wherein the step of forming the dental implant includes the step of forming the enossal sections to have a rotationally asymmetrical geometry that corresponds to the shape of the cavity.

18. The method of claim 17, wherein each of the plurality of rotationally symmetrical geometric bodies is cylindrical in form with a cone-shaped tip and wherein the shape of the enossal sections corresponds to a shape obtained when the axes of symmetry of the plurality of rotationally symmetrical geometric bodies are spaced apart in the form of a polygon with n number of edges.

* * * * *